United States Patent
Jenison

(10) Patent No.: US 10,391,320 B2
(45) Date of Patent: Aug. 27, 2019

(54) TECHNIQUES FOR DETECTING MAGNETIC RESONANCE IMAGING FIELD

(75) Inventor: Troy A. Jenison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1125 days.

(21) Appl. No.: 13/046,158

(22) Filed: Mar. 11, 2011

(65) Prior Publication Data

US 2012/0194191 A1    Aug. 2, 2012

Related U.S. Application Data

(60) Provisional application No. 61/437,419, filed on Jan. 28, 2011.

(51) Int. Cl.
*A61N 1/37* (2006.01)
*G01R 33/28* (2006.01)

(52) U.S. Cl.
CPC .......... *A61N 1/3718* (2013.01); *G01R 33/285* (2013.01); *G01R 33/288* (2013.01)

(58) Field of Classification Search
CPC ...... A61N 1/37; A61N 1/3718; G01R 33/288; G01R 33/285
See application file for complete search history.

(56) References Cited

U.S. PATENT DOCUMENTS

| | | | |
|---|---|---|---|
| 5,438,990 A | 8/1995 | Wahlstrand et al. | |
| 5,545,187 A | 8/1996 | Bergström et al. | |
| 5,629,622 A | 5/1997 | Scampini | |
| 5,662,694 A | 9/1997 | Lidman et al. | |
| 5,697,958 A | 12/1997 | Paul et al. | |
| 5,709,225 A | 1/1998 | Budgifvars et al. | |
| 5,722,998 A | 3/1998 | Prutchi et al. | |
| 6,101,417 A | 8/2000 | Vogel et al. | |
| 6,209,764 B1 | 4/2001 | Hartlaub et al. | |
| 6,437,561 B1 | 8/2002 | Bartingale et al. | |
| 6,510,345 B1 | 1/2003 | Van Bentem | |
| 6,522,920 B2 | 2/2003 | Silvian et al. | |
| 6,580,947 B1 | 6/2003 | Thompson | |

(Continued)

FOREIGN PATENT DOCUMENTS

| | | |
|---|---|---|
| CN | 1762510 | 4/2006 |
| EP | 1493460 A1 | 1/2005 |

(Continued)

OTHER PUBLICATIONS

English translation of JP2007285865; Megumi et al.; Nov. 2007.*

(Continued)

*Primary Examiner* — Michael J Carey
*Assistant Examiner* — Shahdeep Mohammed

(57) ABSTRACT

A device includes a housing, a first magnetic field sensor, a second magnetic field sensor, and a control module. The housing is configured to be implanted in a patient. The first magnetic field sensor is located at a first location within the housing and is configured to measure a first strength of a magnetic field at the first location. The second magnetic field sensor is located at a second location within the housing and is configured to measure a second strength of the magnetic field at the second location. The control module is configured to identify a source of the magnetic field based on the first and second strengths.

32 Claims, 8 Drawing Sheets

(56) References Cited

U.S. PATENT DOCUMENTS

| | | | |
|---|---|---|---|
| 6,839,596 B2 | 1/2005 | Nelson et al. | |
| 6,937,906 B2 * | 8/2005 | Terry | A61N 1/3718 607/63 |
| 6,963,779 B1 | 11/2005 | Shankar | |
| 6,965,792 B2 | 11/2005 | Avrin et al. | |
| 7,016,730 B2 | 3/2006 | Ternes | |
| 7,050,855 B2 | 5/2006 | Zeijlemaker et al. | |
| 7,076,283 B2 | 7/2006 | Cho et al. | |
| 7,174,202 B2 | 2/2007 | Bladen et al. | |
| 7,231,251 B2 | 6/2007 | Younce et al. | |
| 7,239,134 B2 | 7/2007 | McClure et al. | |
| 7,369,898 B1 * | 5/2008 | Kroll | A61B 5/055 600/411 |
| 7,509,167 B2 | 3/2009 | Stessman | |
| 7,561,915 B1 * | 7/2009 | Cooke | A61B 5/055 607/31 |
| 7,639,006 B2 | 12/2009 | Deffeyes | |
| 7,672,726 B2 | 3/2010 | Ginggen | |
| 8,014,856 B2 | 9/2011 | Wedan | |
| 8,121,678 B2 | 2/2012 | Linder et al. | |
| 8,200,334 B1 | 6/2012 | Min et al. | |
| 8,768,486 B2 | 7/2014 | Gray et al. | |
| 8,805,496 B2 | 8/2014 | Ellingson | |
| 2003/0144704 A1 | 7/2003 | Terry et al. | |
| 2004/0088012 A1 * | 5/2004 | Kroll | A61N 1/3718 607/9 |
| 2006/0173295 A1 | 8/2006 | Zeijlemaker | |
| 2006/0276850 A1 | 12/2006 | Deffeyes | |
| 2007/0173890 A1 | 7/2007 | Armstrong | |
| 2007/0173910 A1 | 7/2007 | Armstrong | |
| 2008/0154342 A1 | 6/2008 | Digby et al. | |
| 2008/0154346 A1 | 6/2008 | Smith et al. | |
| 2008/0221638 A1 | 9/2008 | Wedan et al. | |
| 2008/0228092 A1 | 9/2008 | Wedan | |
| 2009/0096413 A1 | 4/2009 | Partovi et al. | |
| 2009/0138058 A1 | 5/2009 | Cooke et al. | |
| 2009/0157146 A1 | 6/2009 | Linder et al. | |
| 2009/0204182 A1 * | 8/2009 | Ameri | A61N 1/3718 607/63 |
| 2009/0210025 A1 | 8/2009 | Ameri | |
| 2009/0237073 A1 | 9/2009 | Uchiyama et al. | |
| 2010/0106227 A1 | 4/2010 | Min et al. | |
| 2010/0137946 A1 | 6/2010 | Gadagkar et al. | |
| 2010/0152805 A1 | 6/2010 | Zeijlemaker | |
| 2010/0176808 A1 | 7/2010 | Legay | |
| 2010/0211123 A1 | 8/2010 | Stubbs et al. | |
| 2010/0292759 A1 | 11/2010 | Hahn et al. | |
| 2011/0092799 A1 * | 4/2011 | Steckner | A61N 1/3718 600/411 |
| 2011/0148365 A1 | 6/2011 | Doerr | |
| 2011/0148400 A1 | 6/2011 | Doerr et al. | |
| 2011/0152667 A1 | 6/2011 | Doerr et al. | |
| 2011/0160565 A1 * | 6/2011 | Stubbs | A61N 1/37 600/411 |
| 2011/0160786 A1 | 6/2011 | Stubbs et al. | |
| 2011/0202104 A1 | 8/2011 | Butala | |
| 2012/0053652 A1 * | 3/2012 | Dianaty | A61N 1/08 607/30 |
| 2012/0105059 A1 | 5/2012 | Doerr et al. | |

FOREIGN PATENT DOCUMENTS

| | | |
|---|---|---|
| EP | 1935450 A1 | 6/2008 |
| JP | H08-334570 | 12/1996 |
| JP | 2007-285865 | 11/2007 |
| JP | 2007-289670 | 11/2007 |
| WO | 02103651 A1 | 12/2002 |
| WO | 2006081434 A1 | 8/2006 |
| WO | 2006124481 A2 | 11/2006 |
| WO | 2010039877 A1 | 4/2010 |
| WO | 2010087866 A1 | 8/2010 |
| WO | 2010096138 A1 | 8/2010 |
| WO | 2011051955 A2 | 5/2011 |
| WO | 2011100241 A1 | 8/2011 |
| WO | 2012102744 A1 | 8/2012 |

OTHER PUBLICATIONS

U.S. Appl. No. 61/437,419, by Troy Jenison, entitled "Techniques for Detecting Magnetic Resonance Imaging Field", filed Jan. 28, 2011.

International Search Report and Written Opinion of international application No. PCT/US2011/034321, dated Sep. 30, 2011, 13 pp.

Office Action from JP Patent Application No. 2013-551957, dated Apr. 9, 2015, 4 pages.

Office Action from CN Patent Application No. 201380022239.2, dated Aug. 31, 2015, 12 pages.

Office Action from JP Patent Application No. 2013-551957 and translation, dated Dec. 3, 2015, 5 pages.

\* cited by examiner

TECHNIQUES FOR DETECTING MAGNETIC RESONANCE IMAGING FIELD

This application claims the benefit of U.S. Provisional Application No. 61/437,419, entitled, "TECHNIQUES FOR DETECTING MAGNETIC RESONANCE IMAGING FIELD," and filed on Jan. 28, 2011, the entire content of which is incorporated herein by reference.

TECHNICAL FIELD

The disclosure relates to techniques for detecting magnetic resonance imaging (MRI) devices, and more particularly, to implantable medical devices capable of detecting MRI fields.

BACKGROUND

Magnetic resonance imaging (MRI) is a medical imaging technique used to visualize detailed internal structures of a patient. A patient is placed at least partially within an MRI device during an MRI scan. The MRI device may generate a variety of magnetic and electromagnetic fields, including a static magnetic field (hereinafter "static MRI field"), gradient magnetic fields, and radio frequency (RF) fields. The static MRI field may be generated by a primary magnet within the MRI device and may be present prior to initiation of the MRI scan. The gradient magnetic fields may be generated by electromagnets and may be present during the MRI scan. The RF magnetic fields may be generated by transmitting/receiving coils and may be present during the MRI scan. If the patient undergoing the MRI scan has an implantable medical device (IMD), the various fields produced by the MRI device may interfere with the operation of the IMD.

SUMMARY

To reduce the effects that the various fields produced during an MRI scan have on IMDs, some IMDs may be programmed to an MRI-compatible mode of operation (also referred to herein as an MRI operating mode) during the MRI scan. Typically, a clinician may program these IMDs using a programming device at some point in time prior to a scheduled MRI scan. After the patient receives the MRI scan, the clinician may reprogram the IMD back to normal settings. The reprogramming process undertaken prior to, and after, scanning a patient with an IMD may be inconvenient to both the patient and the clinician. In some scenarios, a patient having an IMD may require an emergency MRI scan. Such scenarios may not provide an adequate window of time around the MRI scan to allow for reprogramming of the IMD.

An IMD according to the present disclosure may automatically detect the presence of an MRI device (e.g., by detection of the static MRI field) prior to initiation of an MRI scan. For example, the IMD may detect the MRI device based on the spatial gradient and/or strength of the static MRI field. Furthermore, the IMD may differentiate the static MRI field from other magnetic fields, such as magnetic fields generated by handheld magnetic devices such as telemetry head magnets or other handheld magnets, thus improving the specificity with which the IMD identifies the source of a detected magnetic field based on the spatial gradient and/or strength of the detected field.

In response to detection of the MRI device, the IMD may transition from a normal operating mode to an MRI operating mode prior to initiation of the MRI scan. While operating in the MRI mode, the IMD may be configured such that it is less susceptible to being adversely affected by the gradient and RF fields emitted by the MRI device. The capability of the IMD to automatically detect the MRI device and transition to the MRI mode may eliminate the need for manual reprogramming of the IMD prior to the MRI scan, or provide a failsafe reprogramming mode in the event manual reprogramming is not undertaken.

In some examples according to the present disclosure, a device comprises a housing, a first magnetic field sensor, a second magnetic field sensor, and a control module. The housing is configured to be implanted in a patient. The first magnetic field sensor is located at a first location within the housing and is configured to measure a first strength of a magnetic field at the first location. The second magnetic field sensor is located at a second location within the housing and is configured to measure a second strength of the magnetic field at the second location. The control module is configured to identify a source of the magnetic field based on the first and second strengths.

In other examples according to the present disclosure, a method comprises measuring a first strength of a magnetic field at a first location within an implantable device, measuring a second strength of the magnetic field at a second location within the implantable device, and identifying a source of the magnetic field based on the first and second strengths.

In other examples according to the present disclosure, a system comprises an implantable medical device (IMD), a first magnetic field sensor, a second magnetic field sensor, and a control module. The first magnetic field sensor is connected to the IMD and is configured to measure a first strength of a magnetic field at a first location. The second magnetic field sensor connected to the IMD and is configured to measure a second strength of the magnetic field at a second location. The control module is configured to identify a source of the magnetic field based on the first and second strengths.

In other examples according to the present disclosure, a computer-readable storage medium comprises instructions that cause a programmable processor to measure a first strength of a magnetic field at a first location within an implantable device, measure a second strength of the magnetic field at a second location within the implantable device, and identify a source of the magnetic field based on the first and second strengths.

The details of one or more examples are set forth in the accompanying drawings and the description below. Other features, objects, and advantages will be apparent from the description and drawings, and from the claims.

DETAILED DESCRIPTION

Figure 1:
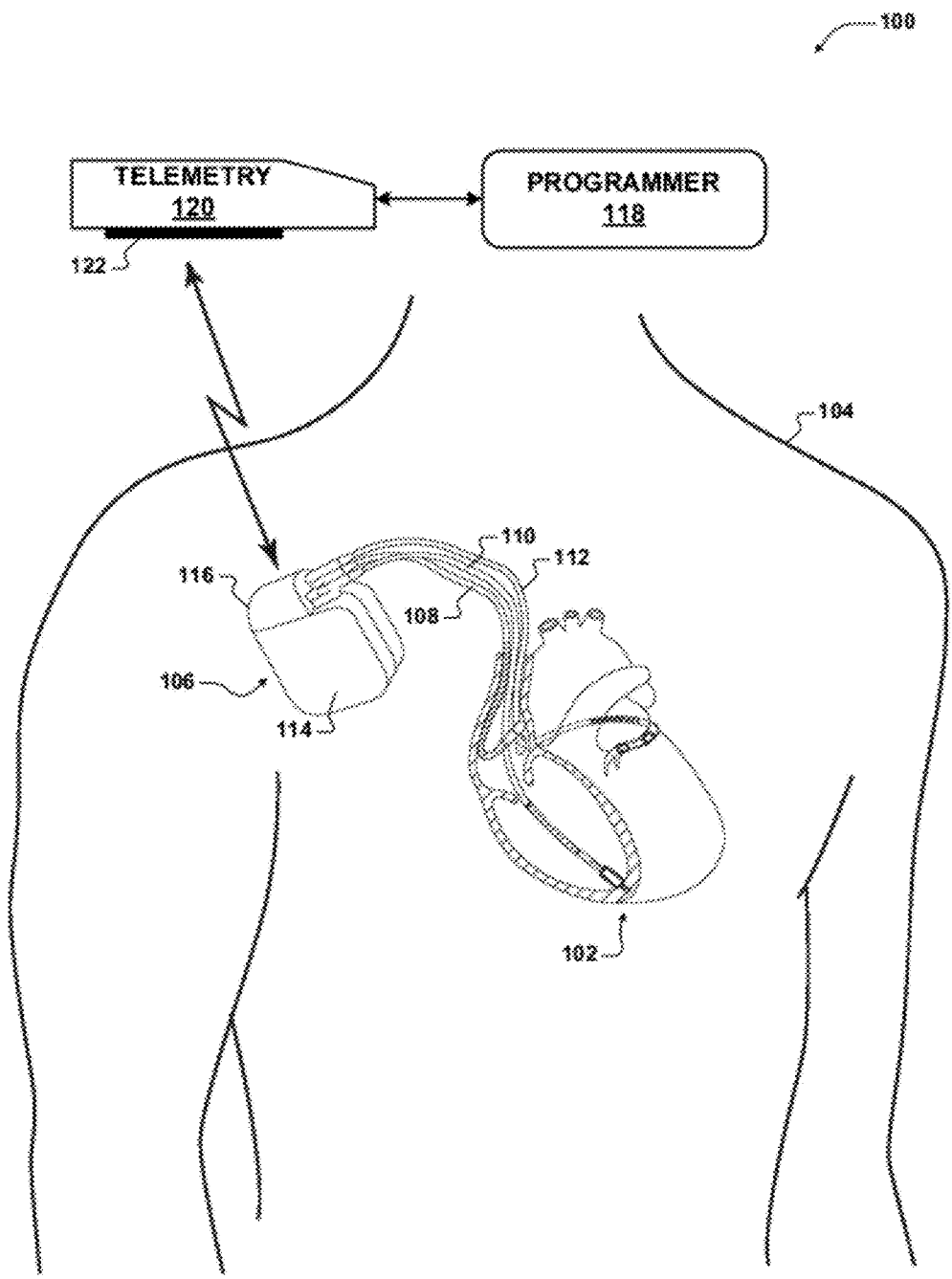
FIG. 1 is a conceptual diagram of an example system comprising an implantable medical device (IMD) for delivering stimulation therapy to a heart of a patient via implantable leads.

An IMD according to the present disclosure may detect a magnetic field and identify the source of the detected magnetic field. For example, the IMD may identify the source of the magnetic field as one of a primary magnet of an MRI device or a telemetry head magnet.

An IMD, described herein as a pacemaker and/or cardioverter/defibrillator, includes a plurality of magnetic field sensors. The IMD may detect the presence of a static MRI field (e.g., the presence of the primary magnet) based on signals received from the plurality of magnetic field sensors. In some examples, the IMD may detect the presence of the static MRI field based on a strength of the detected magnetic field since the strength of the static MRI field may be stronger than that which is producible by a telemetry head magnet. Accordingly, in some examples, the IMD may identify the source of the detected magnetic field as the MRI device when the detected magnetic field is stronger than a field that is typically producible by a telemetry head magnet.

In some scenarios, however, the strength of the static MRI field may be similar to other magnetic fields, e.g., a field generated by a telemetry head magnet of a programmer (i.e., a "telemetry head field"). For example, a telemetry head field may have a similar strength as a static MRI field, depending on the location of the IMD relative to the fields. In some examples, the strength of the telemetry head field in close proximity to the telemetry head magnet may be in the range of strengths exhibited at a distance outside of the bore of an MRI device. Accordingly, because the strength of the static MRI field and the strength of the telemetry head field may be equal in some examples, the static MRI field and the telemetry head field may not be differentiated from one another based on strength alone.

In examples where the telemetry head field and the static MRI field may be roughly equal in strength, the telemetry head field and the static MRI field may exhibit different spatial gradients. The IMD of the present disclosure may differentiate between the telemetry head field and the static MRI field based on this difference in spatial gradients. A spatial gradient of a magnetic field, as used herein, refers to the difference in strength exhibited by a magnetic field at different locations within the magnetic field, e.g., a difference in strength between two points in a magnetic field. The spatial gradient of the telemetry head field may be greater than the spatial gradient of the static MRI field when the strengths of the two fields are in the same range. A greater spatial gradient corresponds to a greater change in magnetic field strength between two points, whereas a smaller spatial gradient corresponds to a smaller change in magnetic field strength between the same two points.

The IMD may determine the strength of a magnetic field at different locations within the IMD based on measurements from the plurality of magnetic field sensors included in the IMD. Subsequently, the IMD may determine a spatial gradient of the detected magnetic field, e.g., by comparing the strengths measured at the different locations. Based on the determined spatial gradient, the IMD may differentiate between the telemetry head field and the static MRI field. For example, the IMD may identify the source of the detected magnetic field as the telemetry head magnet when the determined spatial gradient is greater than a spatial gradient threshold, while the IMD may identify the source of the magnetic field as the MRI device when the determined spatial gradient is less than the spatial gradient threshold. As such, the techniques of this disclosure enable the IMD to have improved sensitivity and specificity as to the source of a detected magnetic field.

The IMD may transition from operation in a "normal mode" to operation in an "MRI mode" or a "telemetry head mode" depending on what the IMD identifies as the source of the magnetic field. In the absence of a magnetic field, the IMD may operate in the normal mode. Operation of the IMD in the normal mode may describe a typical operating state of the IMD, e.g., without detection of a telemetry head, MRI device, or any other magnetic device. The typical operating state may involve operation of ordinary therapy and/or sensing modes in the IMD. In the case of an IMD functioning as an implantable cardioverter-defibrillator, for example, the normal mode may permit normal sensing to support normal pacing, cardioversion and/or defibrillation therapy functions.

The IMD may operate in the telemetry head mode when the IMD identifies the source as the telemetry head magnet. Operation of the IMD in the telemetry head mode may describe a typical operating state of the IMD in response to detection of a telemetry head magnet. For example, after the IMD detects the telemetry head magnet, the IMD may enter the telemetry head mode and may communicate with a programmer by wireless telemetry via a telemetry head, or also via distance telemetry, to transfer data to the programmer and/or receive operating parameters from the programmer. The IMD may also disable tachycardia detection in the telemetry head mode.

The IMD may transition to the MRI mode when the IMD identifies the source of the magnetic field as the MRI device. Operation of the IMD in the MRI mode may describe an operating state of the IMD in which the undesirable effects that may be caused by the gradient magnetic fields and RF fields may be reduced, and possibly eliminated. When operating in the MRI operating mode, the IMD is configured to operate with different functionality compared to the normal operating mode and the telemetry head mode. In some instances, the IMD is configured to operate with reduced functionality compared to the normal operating mode. For example, the IMD may not provide sensing, not deliver therapy, deliver only a subset of possible therapies, not log collected data, or the like.

In some examples, while operating in the MRI mode, the IMD may operate in an asynchronous mode in which pacing is provided according to a set timing and is not responsive to sensed cardiac events. Operation in the asynchronous mode may prevent pacing inhibition due to oversensing that causes identification of electrical noise on the leads as cardiac activity. In other examples, the IMD may turn off pacing in the MRI mode. When the IMD includes defibrillation functionality, the IMD may disable tachycardia detection, disable charging of high voltage capacitor circuits, and disable defibrillation.

Additionally, or alternatively, the IMD may disable diagnostics storage such as cardiac electrogram (EGM) waveform storage, since the MRI fields may corrupt the EGM waveforms. In other instances, the IMD is configured to operate with approximately the same functionality or even increased functionality compared to the normal operating mode. For example, the IMD may use a different sensor (e.g., pressure or acceleration sensor), different sense circuitry, or different sense algorithms to detect cardiac activity of the patient. In some examples, the IMD may function to filter out signals induced by the MRI fields. In some examples, while operating in the MRI mode, the IMD may notify a clinician that the IMD has detected the MRI field and that the IMD is configured for operation during an MRI scan. It is contemplated that the IMD may operate in the MRI mode according to additional settings not described herein in order to ensure proper operation of the IMD during an MRI scan.

FIG. 1 is a conceptual diagram of an example system 100 that may be used to diagnose conditions of and provide therapy to a heart 102 of a patient 104. System 100 includes an IMD 106. For example, IMD 106 may be an implantable pacemaker, cardioverter, and/or defibrillator that provides electrical stimulation to heart 102.

IMD 106 detects the presence of a static MRI field of an MRI device (not shown). In response to detection of the static MRI field, IMD 106 may operate in the MRI mode. An MRI device may include a patient table on which patient 104 is positioned prior to and during an MRI scan. The MRI device includes a scanning portion that houses the primary magnet of the MRI device that generates the static MRI field, the gradient coils that generate the gradient field, and the RF coils that generate the RF field. During the MRI scan, a portion of patient 104 may be positioned within a bore of the MRI device (the "MRI bore"). While positioned within the MRI bore, the portion of patient 104 being scanned may be surrounded by the primary magnet, gradient coils, and RF coils. Although the structure of MRI devices may vary, it is contemplated that the techniques used herein to detect a static MRI field may be generally applicable to a variety of other MRI device configurations, such as open-sided MRI devices, or other configurations.

IMD 106 is coupled to leads 108, 110, 112. Leads 108, 110, 112 extend into heart 102 of patient 104. IMD 106 may sense electrical activity of heart 102 and/or deliver electrical stimulation to heart 102 via electrodes on leads 108, 110, 112.

IMD 106 includes a housing 114 and a connector block 116. Housing 114 and connector block 116 may form a hermetic seal that protects components of IMD 106. In some examples, housing 114 may comprise a metal or other biocompatible enclosure having separate halves. Connecter block 116 may include electrical feedthroughs, through which electrical connections are made between leads 108, 110, 112 and electronic components included within housing 114. Housing 114 is configured to be implanted in a patient.

Housing 114 may enclose a signal generator module that generates therapeutic stimulation, such as cardiac pacing pulses and cardioversion or defibrillation shocks, as well as an electrical sensing module for monitoring the rhythm of heart 102. Leads 108, 110, 112 are coupled to the signal generator module and the electrical sensing module of IMD 106 via connector block 116. Using the signal generator module and the electrical sensing module, IMD 106 may provide pacing pulses to heart 102 based on the electrical signals sensed within heart 102. IMD 106 may also provide defibrillation and/or cardioversion therapy to heart 102. For example, IMD 106 may detect arrhythmia of heart 102, such as fibrillation of the ventricles, and deliver cardioversion or defibrillation therapy to heart 102 in the form of electrical pulses.

System 100 includes a programmer 118. Programmer 118 may be a handheld computing device, desktop computing device, a networked computing device, etc. Programmer 118 may include a computer-readable storage medium having instructions that cause a processor of programmer 118 to provide the functions attributed to programmer 118 in the present disclosure.

Programmer 118 may communicate with IMD 106 via a telemetry head 120. Telemetry head 120 includes a telemetry head magnet 122. Telemetry head magnet 122 generates a magnetic field ("telemetry head field"). IMD 106 may detect the presence of telemetry head magnet 122 (i.e., telemetry head field) and may operate in the telemetry head mode in response to detection of telemetry head magnet 122. In the telemetry head mode, IMD 106 and programmer 118 may communicate with one another, e.g., transfer data between one another. For example, when IMD 106 operates in the telemetry head mode, IMD 106 may send data to programmer 118, and programmer 118 may retrieve data stored in IMD 106 and/or program IMD 106.

In some examples, telemetry head magnet 122 may include a permanent magnet. The permanent magnet may have an area that is approximately equal to the area of IMD 106 so that when telemetry head 120 is placed over top of IMD 106, the permanent magnet may cover IMD 106. In some examples, telemetry head magnet 122 may include handheld magnetic devices other than a permanent magnet, such as an electromagnet that generates the telemetry head field.

Although detection of telemetry head magnet 122 is described herein, the relatively large spatial gradient of the telemetry head field (e.g., relative to the static MRI spatial gradient) may be exhibited by other magnetic fields generated by handheld magnetic devices. For example, a patient magnet (e.g., a handheld permanent magnet) not included in a telemetry head may generate a spatial gradient similar to that generated by telemetry head magnet 122. Additionally, other devices that generate magnetic fields similar to telemetry head magnet 122 may come in proximity to IMD 106. Such devices may include, but are not limited to, permanent magnets other than the patient magnet. Telemetry head magnet 122 may, therefore, generally represent any magnetic device (e.g., handheld magnetic device) or other magnetic field source that generates a magnetic field similar to that of telemetry head magnet 122 and IMD 106 may operate in the telemetry head mode in response to magnets that produce fields similar to the telemetry head field in terms of magnetic field strength and spatial gradient. In general, most "environmental" magnetic field sources will exhibit a field similar to that of telemetry head magnet 122, while few magnetic field sources may exhibit a magnetic field in scale as large as the permanent magnet of an MRI device.

Data retrieved from IMD 106 using programmer 118 may include cardiac EGMs stored by IMD 106 that indicate electrical activity of heart 102. Data may also include marker channel data that indicates the occurrence and timing of sensing, diagnosis, and therapy events associated with IMD 106. Additionally, data may include information regarding the performance or integrity of IMD 106 or other components of diagnostic system 100, such as leads 108, 110, 112, or a power source of IMD 106.

Data transferred to IMD 106 using programmer 118 may include, for example, values for operational parameters, electrode selections used to deliver defibrillation pulses, waveform selections used for defibrillation pulses, and/or configuration parameters for detection algorithms. Programmer 118 may also transfer lower, upper, and spatial gradient threshold values described herein with respect to FIG. 3. These upper, lower, and spatial gradient threshold values may be programmable values that may be calibrated on a patient-by-patient basis, e.g., based on the type of IMD or the location/orientation of the IMD within the patient. In other examples, the values may be programmable in order to provide for compatibility with the variety of MRI devices available on the market, since different MRI devices may present different magnetic field characteristics.

IMD 106 and programmer 118 may communicate via wireless communication using any techniques known in the art. Examples of communication techniques may include, for example, low frequency or RF telemetry, although other techniques are also contemplated.

Although not illustrated in FIG. 1, system 100 may include a patient monitor. The patient monitor may be a handheld computing device, desktop computing device, a networked computing device, or the like, that includes similar functionality as programmer 118. For example, the patient monitor may be a device that reads data from IMD 106 and uploads the data to a server, e.g., automatically or in response to a command from a patient or other user. Programmer 118 and the patient monitor may, but typically will not, be co-located. For example, programmer 118 may be used by a clinician in a clinical setting to communicate with IMD 106, and the patient monitor may communicate with IMD 106 in a patient's home, automatically or in response to a user command.

Although IMD 106 is illustrated as an implantable cardiac stimulation device (e.g., a pacemaker/cardioverter-defibrillator), in other examples, an implantable device that detects the static MRI field and operates in the MRI mode according to the present disclosure may include an implantable drug pump or an implantable neurostimulator that provides at least one of deep brain stimulation, vagus nerve stimulation, gastric stimulation, pelvic floor stimulation, spinal cord stimulation, or other stimulation. In other examples, an implantable device that detects the static MRI field and operates in the MRI mode may include any other active implantable medical device that includes electronics used to provide therapy to a patient. In other examples, a device that detects the static MRI field and operates in the MRI mode may include an external device.

Figure 2A:
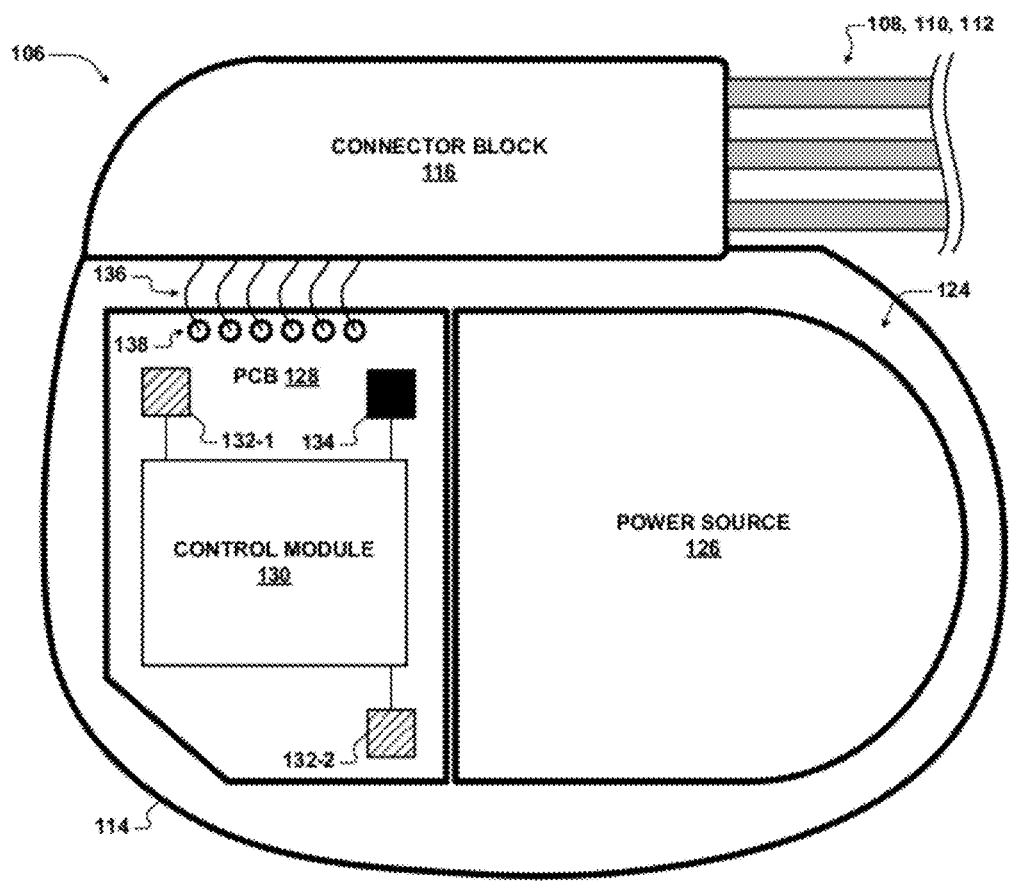
FIGS. 2A and 2B show schematic views of the IMD.
Figure 2B:
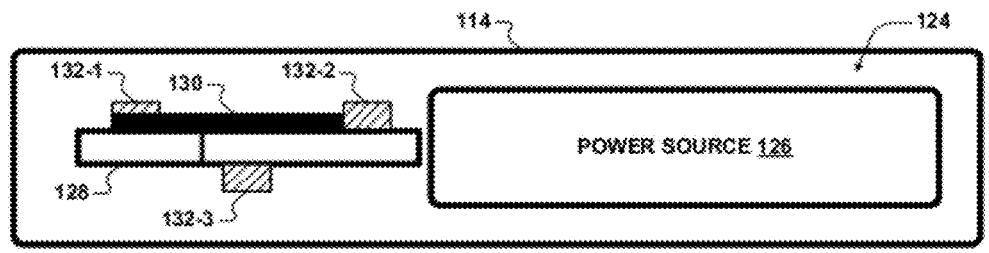

FIGS. 2A-2B show schematic views of IMD 106. The schematic views of IMD 106 illustrate components of IMD 106 within housing 114. Housing 114 defines a cavity 124 in which components of IMD 106 are housed. FIG. 2B shows the arrangement of components within housing 114 from the bottom side of IMD 106 as illustrated in FIG. 2A.

IMD 106 includes a power source 126 housed within cavity 124. Power source 126 may include a battery, e.g., a rechargeable or non-rechargeable battery. IMD 106 includes a printed circuit board (PCB) 128 that includes electronic components of IMD 106. Electronic components include, but are not limited to, a control module 130, first, second, and third magnetic field sensors 132-1, 132-2, 132-3 (collectively "magnetic field sensors 132"), and additional sensor 134 (e.g., a sensor other than a magnetic field sensor).

PCB 128 may not be limited to typical PCB structures, but may instead represent any structure within IMD 106 that is used to mechanically support and electrically connect control module 130, magnetic field sensors 132, power source 126, and other electronic components within housing 114. In some examples, PCB 128 may include one or more layers of conductive traces and conductive vias that provide electrical connection between control module 130 and magnetic field sensors 132.

PCB 128 may provide electrical connections between power source 126, control module 130, and magnetic field sensors 132 such that power source 126 provides power to control module 130 and magnetic field sensors 132. Leads 108, 110, 112 may be connected to control module 130 on PCB 128 through connecting wires 136. For example, connecting wires 136 may be connected to leads 108, 110, 112 at one end, and connected to PCB connection points 138 on PCB 128 at the other end.

Although the electronics components of IMD 106 are illustrated as included on a single PCB, it is contemplated that the electronic components described herein may be included elsewhere within IMD 106, e.g., on other supporting structures within IMD 106, such as additional PCBs (not shown). In other examples, electronic components within IMD 106 may be mounted to the inside of housing 114 within cavity 124 or mounted to the outside of housing 114 and connected to components on the inside of housing 114 through a feedthrough (not shown) in housing 114. In still other examples, electronic components may be mounted on or within connector block 116 or connected to one or more of leads 108, 110, 112.

Control module 130, and modules included within control module 130, represents functionality that may be included in IMD 106 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Each of magnetic field sensors 132 may measure the strength and direction of a magnetic field and generate signals that indicate the strength and the direction of the magnetic field. First magnetic field sensor 132-1 may generate a signal that indicates a strength and direction of a magnetic field that permeates (i.e., passes through) first magnetic field sensor 132-1. In other words, first magnetic field sensor 132-1 may generate a signal that indicates a strength and direction of a magnetic field at the location of first magnetic field sensor 132-1. In a similar manner, second and third magnetic field sensors 132-2, 132-3 may generate signals that indicate the strength and direction of magnetic fields at the locations of second and third magnetic field sensors 132-2, 132-3, respectively.

Control module 130 may receive signals from magnetic field sensors 132 and determine the strength and direction of magnetic fields measured by each of magnetic field sensors 132. For example, control module 130 may determine a strength and direction of a magnetic field at the location of first, second, and third magnetic field sensors 132-1, 132-2, 132-3 based on signals received from first, second, and third magnetic field sensors 132-1, 132-2, 132-3, respectively.

Magnetic field sensors 132 of the present disclosure may represent any type of magnetic field sensor capable of measuring a strength, and in some examples direction, of a magnetic field and generating signals that indicate the strength of the magnetic field. For example, magnetic field sensors 132 may represent one or more types of magnetic field sensors that may include, but are not limited to, Hall-effect sensors, giant magnetoresistance (GMR) based sensors, anisotropic magnetoresistance (AMR) based sensors, tunneling magnetoresistance (TMR) based sensors, or any other type of suitable magnetic field sensor.

Each of magnetic field sensors 132 may include one or more axes of sensitivity. For example, magnetic field sensors 132 may include one axis, two axes, or three axes of sensitivity, and, therefore, magnetic field sensors 132 may indicate the strength and direction of magnetic fields along one, two, or three axes. In some examples, each of magnetic field sensors 132 may be single axis sensors. In other examples, each of magnetic field sensors 132 may be multi-axis sensors, e.g., each of magnetic field sensors 132 may be sensitive to magnetic fields in two or more axes. In still other examples, some of magnetic field sensors 132 may be multi-axis sensors, while the remaining ones of magnetic field sensors 132 may be single axis sensors.

It is contemplated that various configurations and numbers of magnetic field sensors may be implemented within IMD 106. Although 3 magnetic field sensors 132 are illustrated, IMD 106 may include more or less than 3 magnetic field sensors. In some examples, IMD 106 may only include 2 magnetic field sensors, while in other examples, IMD 106 may include 4 or more magnetic field sensors.

The configurations of magnetic field sensors, e.g., locations of magnetic field sensors, number of magnetic field sensors, and number of axes per sensor, may be chosen based on various criteria. In general, a greater number of axes of sensitivity per magnetic field sensor may result in more reliable detection of magnetic fields since a magnetic field having any orientation may be detected, whereas a single axis sensor may only measure a single axis component of a magnetic field.

In examples where a single axis sensor is used, magnetic fields having orientations that are not sensed by the single axis sensor may not be measured at the location of the single axis sensor. It therefore follows that in some examples, using multiple three axis sensors as magnetic field sensors may provide the most complete solution to sensing any magnetic field present, regardless of direction. However, multi-axis sensors may be more costly than single axis sensors, may draw more power than single axis sensors, and control module 130 may use more processing power when polling multi-axis sensors and when determining magnetic field direction based on the signals from multi-axis sensors. Accordingly, in some examples, multi-axis sensors and single axis sensors may be arranged within IMD 106 in such a way as to provide for reliable detection the static MRI field while minimizing cost and power dissipation.

Although magnetic field sensors 132-1, 132-2 are illustrated as mounted on the same side of PCB 128 and magnetic field sensor 132-3 is illustrated as mounted on the other side of PCB 128, other arrangements of magnetic field sensors 132 within IMD 106 are contemplated. For example, in IMDs including two magnetic field sensors, the two magnetic field sensors may be included on the same side of a PCB, or on different sides of a PCB. In some examples, the magnetic field sensors may be included on the same integrated circuit substrate and therefore packaged within the same integrated circuit package. In some examples, the magnetic field sensors may be included within integrated circuit packages along with other electronics components, e.g., on substrates with other integrated circuits or packaged with other integrated circuits within a multi-chip package.

IMD 106 may be subjected to various sources of magnetic fields having varying strengths. For example, IMD 106 may be subjected to the telemetry head field or the static MRI field. Control module 130 may identify the source of a detected magnetic field based on signals received from one or more of magnetic field sensors 132. For example, based on the signals received from magnetic field sensors 132, control module 130 may identify the source of a detected magnetic field as the MRI device or telemetry head magnet 122. A processor of control module 130 may then operate in the MRI mode when the source is identified as the MRI device or the telemetry head mode when the source is identified as telemetry head magnet 122.

In some examples, control module 130 may identify the source of the detected magnetic field based only on a strength of the detected magnetic field. In other examples, control module 130 may identify the source of the detected magnetic field based on both a strength of the detected magnetic field and a spatial gradient of the detected magnetic field.

Figure 3:
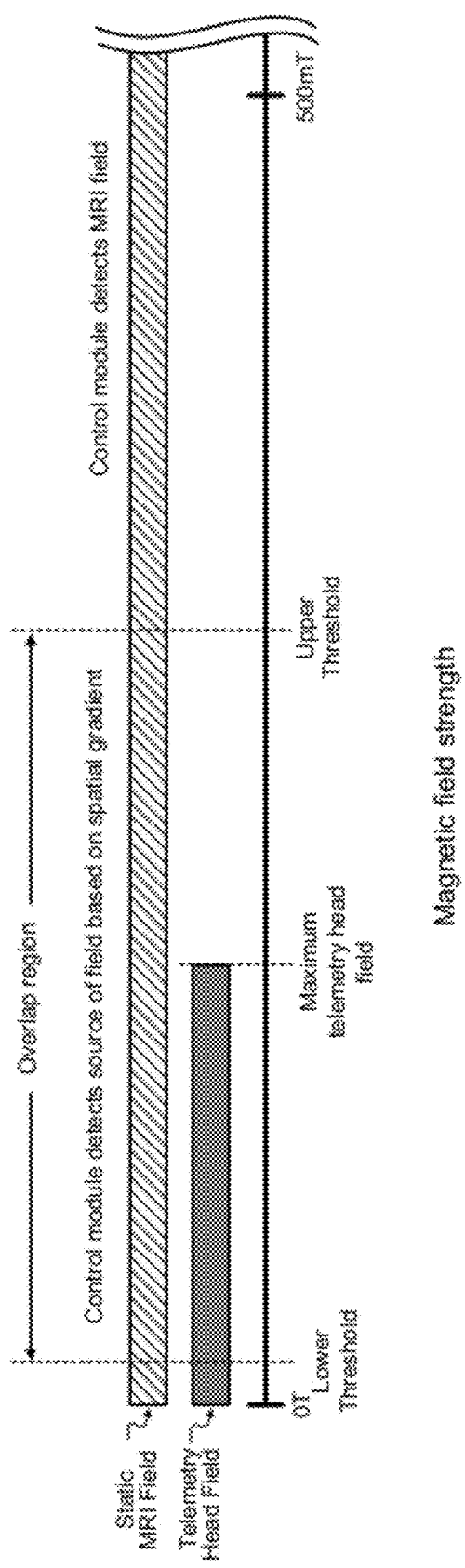
FIG. 3 shows the strength of a static MRI field and a telemetry head field.

The strength and spatial gradients of the static MRI field and telemetry head field are now discussed with reference to FIG. 3. Strength of the telemetry head field (shaded box in FIG. 3) and the static MRI field (hashed box in FIG. 3) are illustrated in FIG. 3, along with user programmable thresholds (e.g., lower/upper thresholds) used by control module 130 to determine the source of detected magnetic fields.

The strength of the telemetry head field may be at a maximum at a point nearest to telemetry head magnet 122. The strength of the telemetry head field may decrease (e.g., exponentially) with increasing distance from telemetry head magnet 122. In FIG. 3, the strength of the telemetry head field is illustrated as ranging from 0 T up to the demarcated "maximum telemetry head field." The "maximum telemetry head field" may be a maximum strength of the telemetry head field, e.g., at a point closest to telemetry head magnet 122.

At a short distance from telemetry head magnet 122 (e.g., within inches), the telemetry head field may drop to a strength of 0-1 mT. For example, within inches (e.g., less than 10 inches), the telemetry head field may drop to less than 0.5 mT. The left edge of the solid shaded region at 0 T indicates a scenario where the telemetry head field is not detectable by magnetic field sensors 132. In other words, the far left edge of the solid shaded region at 0 T indicates a scenario where IMD 106 is positioned relative to telemetry head magnet 122 such that the telemetry head field generated by telemetry head magnet 122 is not detectable by magnetic field sensors 132. As the distance between telemetry head magnet 122 and IMD 106 is decreased, the strength of the telemetry head field detectable by magnetic field sensors 132 may increase up to the maximum telemetry head field.

In some examples, the maximum telemetry head field strength detectable by one of magnetic field sensors 132 may be approximately 100 mT, e.g., when IMD 106 is in close proximity to telemetry head magnet 122. Although the maximum telemetry head field may be approximately 100 mT, in other examples, the maximum telemetry head field may be greater or less than 100 mT.

The strength of the static MRI field may reach a maximum value (e.g., 1.5-3 T) within the MRI bore (e.g., close to the primary magnet) of the MRI device and taper off towards a value of 0 T in areas outside of the MRI bore. Generally, the static MRI field may decrease in strength with increasing distance from the MRI bore. The left edge of the hashed region at 0 T indicates a scenario where the static MRI field is not detectable by magnetic field sensors 132. In other words, the far left edge of the hashed region at 0 T indicates a scenario where IMD 106 is positioned relative to the MRI bore such that the static MRI field generated by the MRI device is not detectable by magnetic field sensors 132. As the distance between the MRI bore and IMD 106 is decreased, the strength of the static MRI field detectable by magnetic field sensors 132 may increase up to the maximum strength of the static MRI field. The far right portion of the hashed region in FIG. 3 illustrates the magnetic field detectable by magnetic field sensors 132 when IMD 106 is positioned near to, or within, the MRI bore. Although not illustrated in FIG. 3, the maximum strength of the static MRI field may be in the range of 1.5-3 T.

The values labeled as "lower threshold" and "upper threshold" in FIG. 3 may be programmable values stored in control module 130 that may be used by control module 130 to identify the source of a detected magnetic field. The lower threshold may be a value indicating a minimum magnetic field strength which control module 130 may identify as either telemetry head magnet 122 or as the MRI device. When the detected magnetic field is weaker than the lower threshold, control module 130 may operate in the normal mode. The lower threshold value may be set to a value that reliably indicates either that telemetry head magnet 122 is near to IMD 106 or that the MRI device is near to IMD 106. In other words, the lower threshold value may be set so that control module 130 ignores magnetic fields that are weaker than may be indicative of telemetry head magnet 122 or the MRI device. The lower threshold value may therefore reject "noise" or other magnetic fields produced by sources other than telemetry head magnet 122 or the MRI device. In some examples, the lower threshold may be set to approximately 1-2 mT.

The upper threshold value indicates a maximum magnetic field strength that control module 130 may recognize as a magnetic field generated by telemetry head magnet 122. Control module 130 may determine that IMD 106 is in the presence of the static MRI field when the detected magnetic field is greater than the upper threshold. For example, the upper threshold value may be set such that the upper threshold value is greater than a magnetic field that is producible by telemetry head magnet 122. Accordingly, detection of a magnetic field above the upper threshold value may indicate with high probability that the detected magnetic field is generated by the MRI device, and not telemetry head magnet 122. Therefore, in examples where control module 130 detects a magnetic field having a strength greater than the upper threshold value, control module 130 may reliably identify the source of the detected magnetic field as the MRI device. Control module 130 may then operate IMD 106 in the MRI mode. In some examples, the upper threshold value may be set to approximately 200-500 mT, e.g., a range of magnetic field strengths not producible by telemetry head magnet 122, or at least not typically producible by telemetry head magnet 122 at a location where IMD 106 is implanted.

In some examples, the upper threshold value may be set at the maximum telemetry head field, or slightly greater (e.g., 1-2 mT greater) than the maximum telemetry head field since any field detected by control module 130 that is greater than the maximum telemetry head field may be presumed to be the static MRI field. However, strength of the telemetry head field may vary amongst telemetry head magnets, and accordingly, in some examples, setting the upper threshold value to a value that is only slightly greater (e.g., by 1-2 mT) than the maximum telemetry head field may not be sufficient to reliably rule out the telemetry head field. Therefore, selection of an upper threshold value that is substantially greater (e.g., by a factor of 2) than may be producible by any telemetry head magnet may result in more reliable detection of the static MRI field based solely on the magnitude of the detected magnetic field at a single location.

As described above, depending on the location of IMD 106 relative to the magnetic field source, the strength of the static MRI field may be similar to the strength of the telemetry head field. For example, when IMD 106 is located a distance away from the MRI bore, e.g., on the order of 1-2 feet, depending on the strength of the permanent magnet, the static MRI field may have a similar strength as fields produced by telemetry head magnet 122 (e.g., 100 mT or less). In examples where control module 130 detects a magnetic field having a magnitude in a range where the static MRI field and the telemetry head field may be equal (e.g., 0-100 mT), control module 130 may not reliably differentiate the static MRI field from the telemetry head field based on the strength of the detected magnetic field at a single location. The range of values between the upper and lower threshold values which includes magnetic field strengths that may be indicative of either the telemetry head field or the static MRI field may be referred to as the "overlap region," as indicated in FIG. 3.

Although the static MRI field and the telemetry head field may have similar strengths in the overlap region, the spatial gradients of the static MRI field and the telemetry head field may differ from each other in the overlap region. For example, at a point near telemetry head magnet 122 (e.g., flush with telemetry head magnet 122), the strength of the telemetry head field may be at a maximum value (e.g., 100 mT). The strength of the telemetry head field may decrease (e.g., exponentially) from the maximum value to 0 T as the distance from telemetry head magnet 122 increases. A difference in strength of the telemetry head field between two locations within the telemetry head field may be referred to as the spatial gradient of the telemetry head field. As another example, at a location near the MRI bore (e.g., within the MRI bore), the strength of the static MRI field may be at a maximum value. The strength of the static MRI field may decrease to 0 T as the distance from the MRI bore increases. At a given distance outside of the MRI bore, the strength of the static MRI field may be similar to that producible by telemetry head magnet 122, as described above. However, at the given distance outside of the MRI bore, the spatial gradient of the MRI field may differ from the spatial gradient of the telemetry head field.

The spatial gradient of the static MRI field may be less than the spatial gradient of the telemetry head field when the strength of the static MRI field is in the overlap region. For example, in the overlap region, a difference in the strength of the static MRI field between two points may be relatively less than the difference in strength exhibited by the telemetry head field between the same two points. As an additional example, for two given points, separated by a distance on the order of the separation distance between two magnetic field sensors, the static MRI field may exhibit a smaller change in magnetic field strength than the telemetry head field in the overlap region. Control module 130 may differentiate between the static MRI field and the telemetry head field in the overlap region based on this difference in spatial gradient of the two fields. Accordingly, control module 130 may identify the source of the detected magnetic field based on the measured spatial gradient in the overlap region.

Control module 130 may determine a spatial gradient of a magnetic field in which IMD 106 is located based on the strengths of the magnetic fields measured by magnetic field sensors 132. For example, control module 130 may determine the spatial gradient based on a difference in strength of a magnetic field as measured by two of magnetic field sensors 132 at different locations.

In general, the range of spatial gradient values that is indicative of the telemetry head field is greater than the range of spatial gradient values that is indicative of the static MRI field. Control module 130 may include a spatial gradient threshold value that reliably demarcates the range of spatial gradient values that indicates the static MRI field and the range of spatial gradient values that indicates the telemetry head field. For example, the spatial gradient threshold value may be selected such that measured spatial gradient values less than the spatial gradient threshold indicate the static MRI field, while spatial gradient values greater than the spatial gradient threshold value indicate the telemetry head field. Control module 130 may use the spatial gradient threshold value in order to differentiate between the static MRI field and the telemetry head field in the overlap region. The spatial gradient threshold value may be set by the user in some examples using programmer 118.

When control module 130 detects a magnetic field having a strength in the overlap region, control module 130 may determine the spatial gradient of the sensed magnetic field. Subsequently, control module 130 may compare the determined spatial gradient to the spatial gradient threshold. Control module 130 may then identify the source of the detected magnetic field as telemetry head magnet 122 when the determined spatial gradient is greater than the spatial gradient threshold. Control module 130 may identify the source of the detected magnetic field as the MRI device when the determined spatial gradient is less than the spatial gradient threshold.

Figure 4:
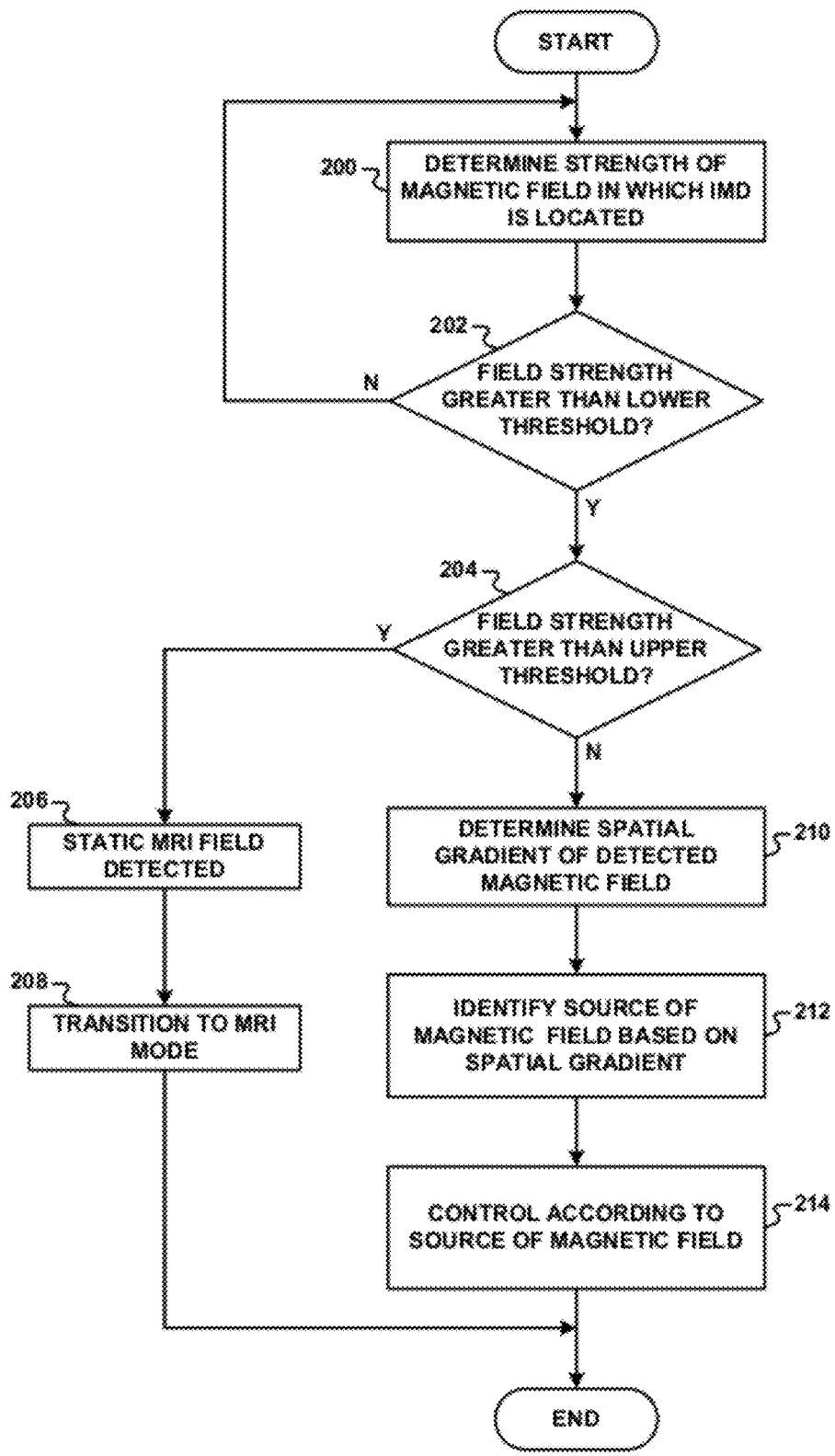
FIG. 4 illustrates an example method for identifying a source of a magnetic field.

FIG. 4 illustrates an example method for identifying a source of a magnetic field according to the present disclosure. Initially, control module 130 may determine the strength of a magnetic field in which IMD 106 is located (200). For example, control module 130 may determine the strength of the magnetic field based on signals received from one or more of magnetic field sensors 132. In one example, control module 130 may determine the strength of the magnetic field at a single location based on signals received from one of magnetic field sensors 132. In other examples, the control module 130 may determine the strength of the magnetic field in which IMD 106 is located based on signals received from more than one of magnetic field sensors 132. For example, control module 130 may determine an average of the strengths detected.

Control module 130 may then determine whether the strength of the magnetic field determined in block (200) is greater than the lower threshold (202). If the strength of the magnetic field determined in block (200) is less than the lower threshold, control module 130 may continue to measure the strength of the magnet field in which IMD 106 is located in block (200) until the strength of the magnetic field detected in block (200) is greater than the lower threshold value. If the strength of the magnetic field determined in block (200) is greater than the lower threshold, control module 130 may determine whether the strength of the magnetic field is greater than the upper threshold (204).

If the strength of the magnetic field is greater than the upper threshold, control module 130 may identify the magnetic field as the static MRI field (206) and control module 130 may transition IMD 106 from operation in the normal mode to operation in the MRI mode to prepare IMD 106 for an MRI scan (208). If the strength of the magnetic field is less than the upper threshold, and therefore between the lower threshold and the upper threshold (i.e., in the overlap region), control module 130 may determine the spatial gradient of the detected magnetic field (210). Control module 130 may determine the spatial gradient of the magnetic field in which IMD 106 is located based on signals received from any two of magnetic field sensors 132. In one example, the magnetic field strength sensed in block (200) may be used as one of the magnetic field strengths used in the calculation of the spatial gradient in block (210). In this example, control module 130 may determine another magnetic field strength at a different location than in block (200), and then subsequently determine the spatial gradient based on the two magnetic field strengths (210).

Control module 130 may then identify the source of the magnetic field based on the spatial gradient (212). Control module 130 may identify the source of the magnetic field as the MRI device when the determined spatial gradient has a value that is less than the spatial gradient threshold. Control module 130 may identify the source of the magnetic field as telemetry head magnet 122 when the determined spatial gradient is greater than the spatial gradient threshold.

After identifying the source of the magnetic field in block (212), control module 130 may take appropriate control action based on the identification (214). For example, control module 130 may transition IMD 106 from operation in the normal mode to operation in the MRI mode when control module 130 identifies the source of the magnetic field as the MRI device, and control module 130 may transition IMD 106 from operation in the normal mode to operation in the telemetry head mode to prepare for communication with telemetry head 120 when control module 130 identifies the source of the magnetic field as telemetry head magnet 122.

Figure 5:
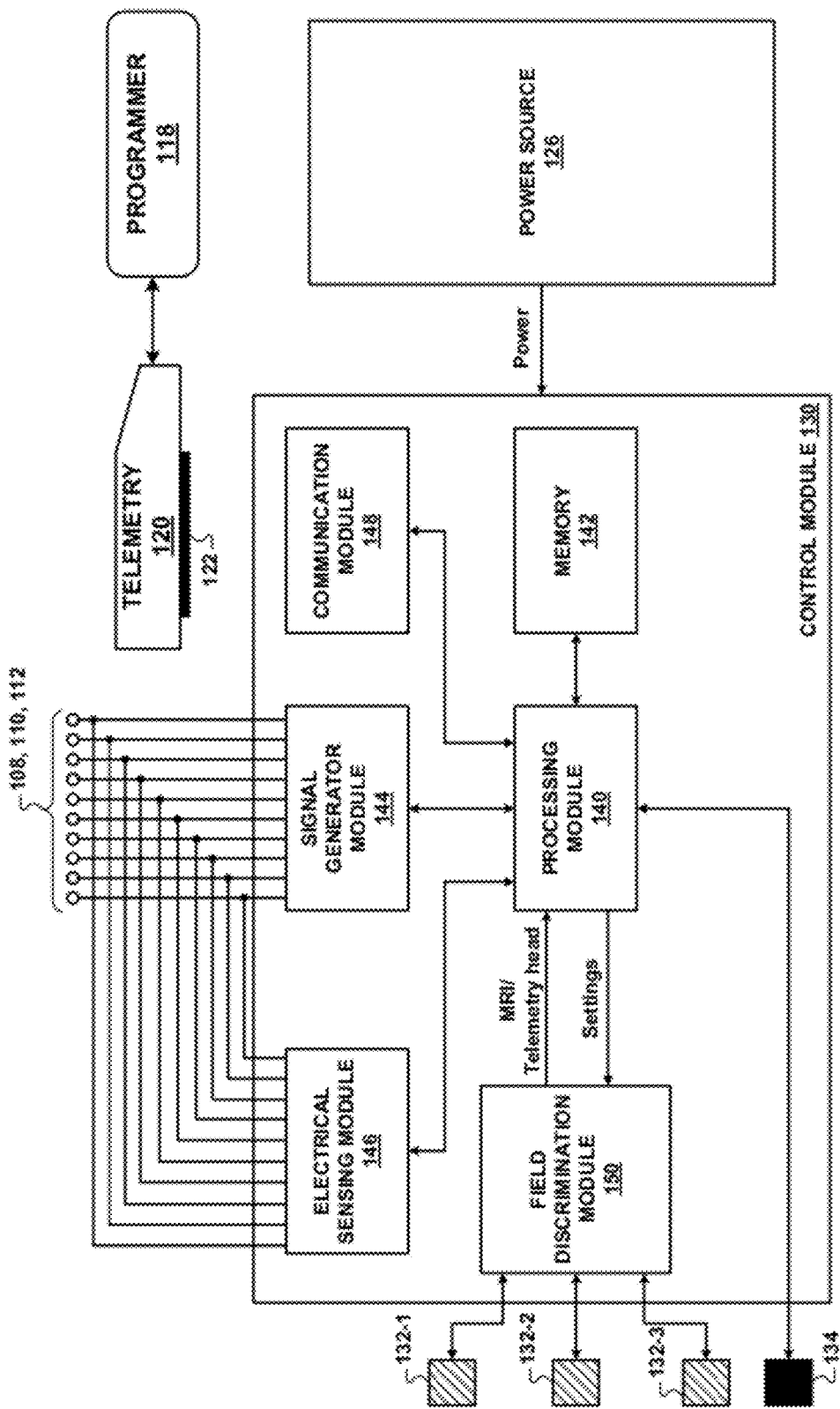
FIG. 5 is a functional block diagram that illustrates an example control module of the IMD.
Figure 6:
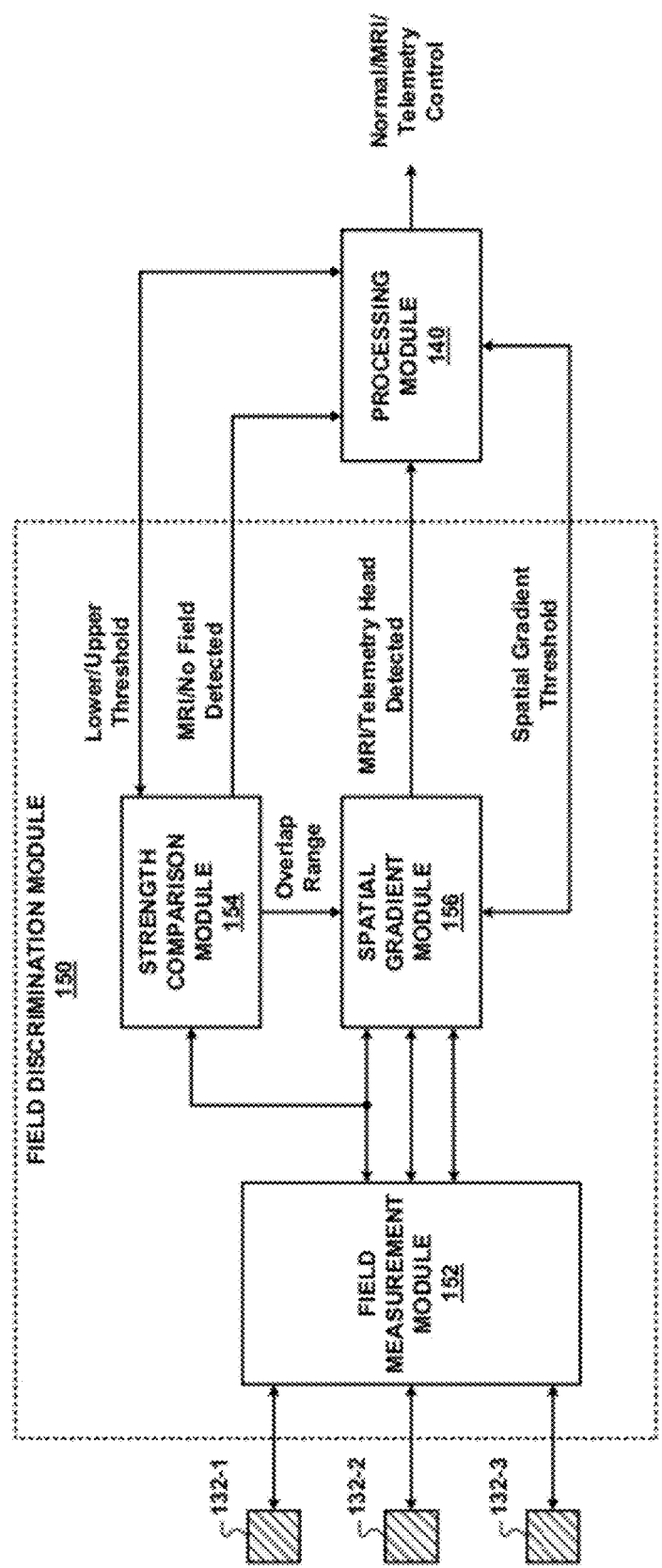
FIG. 6 is a functional block diagram of an example field discrimination module.

FIGS. 5 and 6 are block diagrams that illustrate an example control module 130 of IMD 106. Control module 130 includes a processing module 140, memory 142, a signal generator module 144, an electrical sensing module 146, a communication module 148, and a field discrimination module 150.

Processing module 140 may communicate with memory 142. Memory 142 may include computer-readable instructions that, when executed by processing module 140, cause processing module 140 to perform the various functions attributed to processing module 140 herein. Memory 142 may include any volatile, non-volatile, magnetic, or electrical media, such as RAM, ROM, NVRAM, EEPROM, Flash memory, or any other digital media.

Processing module 140 may communicate with signal generator module 144 and electrical sensing module 146. Signal generator module 144 and electrical sensing module 146 are electrically coupled to electrodes of leads 108, 110, 112. Electrical sensing module 146 is configured to monitor signals from electrodes of leads 108, 110, 112 in order to monitor electrical activity of heart 102, such as the depolarization and repolarization of heart 102. Processing module 140 may detect cardiac activity based on signals received from electrical sensing module 140. In some examples, processing module 140 may detect tachyarrhythmias based on signals received from electrical sensing module 146, e.g., using any suitable tachyarrhythmia detection algorithm.

Processing module 140 may generate EGM waveforms based on the detected cardiac activity. Processing module 140 may also generate marker channel data based on the detected cardiac activity. For example, marker channel data may include data that indicates the occurrence and timing of sensing, diagnosis, and therapy events associated with IMD 106. Additionally, marker channel data may include information regarding the performance or integrity of IMD 106 or other components of diagnostic system 100, such as leads 108, 110, 112, or power source 126. Processing module 140 may store EGM waveforms and marker channel data in memory 142. Processing module 140 may later retrieve stored EGMs from memory 142, e.g., upon a request from programmer 118 via communication module 148.

Signal generator module 144 is configured to generate and deliver electrical stimulation therapy to heart 102. Processing module 140 may control signal generator module 144 to deliver electrical stimulation therapy to heart 102 according to one or more therapy programs, which may be stored in memory 142. For example, processing module 140 may control signal generator module 144 to deliver pacing pulses to heart 102 based on one or more therapy programs and signals received from electrical sensing module 146.

Signal generator module 144 may be configured to generate and deliver cardioversion and defibrillation shocks to heart 102. Processing module 140 may control signal generator module 144 to deliver the cardioversion and defibrillation pulses to heart 102. For example, in the event that processing module 140 detects an atrial or ventricular tachyarrhythmia, processing module 140 may load an anti-tachyarrhythmia pacing regimen from memory 142, and control signal generator module 144 to implement the anti-tachyarrhythmia pacing regimen. Signal generator module 144 may include a high voltage charge circuit and a high voltage output circuit when signal generator module 144 is configured to generate and deliver defibrillation pulses to heart 102.

Communication module 148 includes any suitable hardware, firmware, software or any combination thereof for communicating with another device, such as programmer 118 and/or a patient monitor, e.g., by wireless telemetry. Under the control of processing module 140, communication module 148 may receive downlink telemetry from and send uplink telemetry to programmer 118 and/or a patient monitor with the aid of an antenna (not shown) in IMD 106. Processing module 140 may provide the data to be uplinked to programmer 118 and the control signals for a telemetry circuitry within communication module 148, e.g., via an address/data bus.

In some examples, IMD 106 may include sensors (e.g., additional sensor 134) other than magnetic field sensors 132, with which processing module 140 may communicate. For example, additional sensor 134 may comprise at least one of a motion sensor (e.g., an accelerometer or piezoelectric element), a heart sound sensor, or a pressure sensor (e.g., a capacitive sensor) that senses intracardiac or other cardiovascular pressure. Although illustrated in FIG. 2A as connected to PCB 128, additional sensor 134 may be positioned in various locations in diagnostic system 100. For example, additional sensor 134 may be located within housing 114, outside of housing 114, attached to one or more of leads 108, 110, 112, or wirelessly coupled to control module 130 via communication module 148.

Field discrimination module 150 communicates with magnetic field sensors 132 and processing module 140.

Field discrimination module 150 may include circuits that interface with magnetic field sensors 132. For example, field discrimination module 150 may include circuits that provide power to magnetic field sensors 132 and may also include amplification circuits, filtering circuits, and/or other signal conditioning circuits that process signals received from magnetic field sensors 132. In some examples, field discrimination module 150 may also include circuits that digitize the conditioned signals and communicate the digitized signals to processing module 140.

Field discrimination module 150 receives signals from magnetic field sensors 132 and determines the strength and direction of a magnetic field at the locations of magnetic field sensors 132. Field discrimination module 150 may identify the source of the detected magnetic field as either the MRI device or telemetry head magnet 122 based on the signals received from magnetic field sensors 132. Subsequently, field discrimination module 150 may indicate the source of the detected magnetic field to processing module 140. In examples where no magnetic field is sensed by magnetic field sensors 132, field discrimination module 150 may indicate to processing module 140 that no magnetic field is sensed.

Processing module 140 may transition IMD 106 from operation in the normal mode to operation in one of the telemetry head mode or the MRI mode, depending on the source of the magnetic field indicated by field discrimination module 150. Processing module 140 may operate in the normal mode while no magnetic field is detected. While operating in the normal mode, processing module 140 may provide typical sensing, pacing, and defibrillation functions without preparing for communication with telemetry head 120 or preparing IMD 106 for entry into an MRI scanner. Operation of processing module 140, however, may change when transitioning IMD 106 from operation in the normal mode to operation in either the telemetry head mode or the MRI mode.

Processing module 140 may transition IMD 106 from operation in the normal mode to operation in the telemetry head mode in response to indication from field discrimination module 150 that the source of the magnetic field is telemetry head magnet 122. While in the telemetry head mode, processing module 140 may control communication module 148 to communicate with telemetry head, e.g., download data from telemetry head 120 and upload data to telemetry head 120.

Processing module 140 may transition IMD 106 from operation in the normal mode to operation in the MRI mode in response to indication from field discrimination module 150 that the source of the magnetic field is the MRI device. While in the MRI mode, processing module 140 may execute commands that prepare IMD 106 for exposure to an MRI scan. For example, processing module 140 may notify an operator, via communication module 148, that the MRI field has been detected and that IMD 106 is configured for operation during an MRI scan. In some examples, processing module 140 may control signal generator module 144 to operate in an asynchronous mode in which pacing may be provided according to a set timing, i.e., fixed, predetermined timing, and may not be responsive to events sensed by electrical sensing module 146 such as sensed cardiac P or R waves. When signal generator module 144 includes defibrillator functionality, processing module 140 may disable tachycardia detection and defibrillation in the MRI mode so that any electrical noise induced in leads 108, 110, 112 may not be misinterpreted as a tachycardia event. Processing module 140 may also discontinue storing EGM waveforms in memory 142 and may disable diagnostic functions since the gradient and RF fields may corrupt the EGM waveforms. In some examples, processing module 140 may use sensor 134 (e.g., a pressure or acceleration sensor), different sense circuitry, or different sense algorithms to detect cardiac activity of the patient. In other examples, processing module 140 may instruct electrical sensing module 146 to filter out signals induced by the MRI fields. It is contemplated that processing module 140 may control electrical sensing module 146 and signal generator module 144 according to additional settings not described herein in order to ensure proper operation of IMD 106 during an MRI scan.

Field discrimination module 150 may include programmable settings that are used to identify a detected magnetic field. As described above, the settings may include a lower threshold, an upper threshold, and a spatial gradient threshold. In some examples, a user may program the lower threshold, the upper threshold, and the spatial gradient threshold. In these examples, the user may enter the lower, upper, and spatial gradient thresholds into programmer 118 which may then transfer the lower, upper, and spatial gradient thresholds to processing module 140 via communication module 148. Subsequently, processing module 140 may transfer the lower, upper, and spatial gradient thresholds to field discrimination module 150 for use by field discrimination module 150 in identifying the detected magnetic field. Additionally, in some examples, the user may query the current lower, upper, and spatial gradient thresholds using programmer 118. A more detailed description of field discrimination module 150 is described with reference to the functional block diagram of FIG. 6 and the method of FIG. 7.

In some examples, field discrimination module 150 may include settings for enabling and disabling the MRI field detection function. For example, when enabled, field discrimination module 150 may identify the source of the detected magnetic field as the MRI device or telemetry head magnet 120. When the MRI field detection function is disabled, field discrimination module 150 may not identify the source of the detected magnetic field as the MRI device, but instead may interpret any detected magnetic field as originating from telemetry head magnet 122. The settings for enabling and disabling the MRI field detection function may be programmed into field discrimination module 150 using programmer 118. The settings for enabling and disabling the MRI field detection function may also be queried by the user, for example, using programmer 118.

In some examples, processing module 140 may be configured to indicate, via communication module 148, to an external computing device when the static MRI field is detected. For example, an external computing device may include programmer 118, or any other computing device within the imaging room in which the MRI device is located. Upon detection of the static MRI field, processing module 140 may indicate, via communication module 148, to the external computing device that the patient has an IMD that is capable of detecting the static MRI field and/or that the static MRI field is detected. The external computing device may then display an indicator to a clinician, e.g., on a display, that IMD 106 has detected the MRI device and is prepared for the MRI scan.

As a further example, upon detection of the static MRI field, processing module 140 may indicate, via communication module 148, to the external computing device that the static MRI field is detected. The external computing device may then send an acknowledgement to IMD 106 in response to the indication received from communication module 148. In response to receipt of the acknowledgement, processor 140 may operate IMD 106 in the MRI mode.

FIG. 6 shows a functional block diagram of an example field discrimination module 150. Field discrimination module 150 includes a field measurement module 152 that receives signals from magnetic field sensors 132. Field measurement module 152 receives signals from first magnetic field sensor 132-1 and determines the strength and direction of a magnetic field at the location of first magnetic field sensor 132-1. Field measurement module 152 receives signals from second magnetic field sensor 132-2 and determines the strength and direction of the magnetic field at the location of second magnetic field sensor 132-2. Field measurement module 152 receives signals from third magnetic field sensor 132-3 and determines the strength and direction of the magnetic field at the location of third magnetic field sensor 132-3.

Strength comparison module 154 compares the strength of the magnetic field at the location of first magnetic field sensor 132-1 to the lower and upper thresholds. In cases where no magnetic field is measured by field measurement module 152, or when a magnetic field having a strength that is less than the lower threshold is measured, strength comparison module 154 indicates to processing module 140 that no magnetic field is detected. Processing module 140 may then control IMD 106 in the normal mode in response to the indication.

In the case where field measurement module 152 measures a magnetic field having a strength that is greater than the upper threshold, strength comparison module 154 indicates to processing module 140 that the static MRI field is detected. Processing module 140 may then transition IMD 106 to operation in the MRI mode. In the case where field measurement module 152 measures a magnetic field having a strength between the lower and upper thresholds, strength comparison module 154 determines that the detected magnetic field is in the overlap region. Strength comparison module 154 indicates to spatial gradient module 156 when the detected magnetic field has a strength that falls within the overlap region.

Although strength comparison module 154 is described above as determining the strength of the detected magnetic field based on measurements from a single sensor (e.g., first magnetic field sensor 132-1), in other examples, strength comparison module 154 may determine the strength of the detected magnetic field based on measurements from multiple sensors, e.g., an average field measurement determined based on signals received from a plurality of magnetic field sensors 132.

Spatial gradient module 156 determines the source of the magnetic field measured by field measurement module 152 when the strength of the magnetic field measured by field measurement module 152 is in the overlap region. Spatial gradient module 156 may determine the strength of the detected magnetic field in the location of first magnetic field sensor 132-1 based on measurements made by measurement module 152. Spatial gradient module 156 may determine the strength of the detected magnetic field at different locations other than the location of first magnetic field sensor 132-1 based on measurements made by field measurement module 152 of magnetic field sensors 132 at different locations. For example, spatial gradient module 156 may determine the spatial gradient based on the strength of the magnetic field as sensed by second magnetic field sensor 132-2. In general, spatial gradient module 156 may determine the spatial gradient of the detected magnetic field based on measurement of the detected magnetic field at two locations, e.g., the location of first magnetic field sensor 132-1 (i.e., the first location) and the location of another one of magnetic field sensors 132 (i.e., the second location).

Spatial gradient module 156 may include the spatial gradient threshold. Spatial gradient module 156 may compare the determined spatial gradient to the spatial gradient threshold. In the case where the determined spatial gradient is greater than the spatial gradient threshold, spatial gradient module 156 may indicate to processing module 140 that a telemetry head device is detected, and, in response, processing module 140 may control IMD 106 in the telemetry head mode. In the case where the determined spatial gradient is less than the spatial gradient threshold, spatial gradient module 156 may indicate that an MRI device is detected and, in response, processing module 140 may control IMD 106 in the MRI mode. In other cases, processing module 140 may control IMD 106 in the normal mode.

Figure 7:
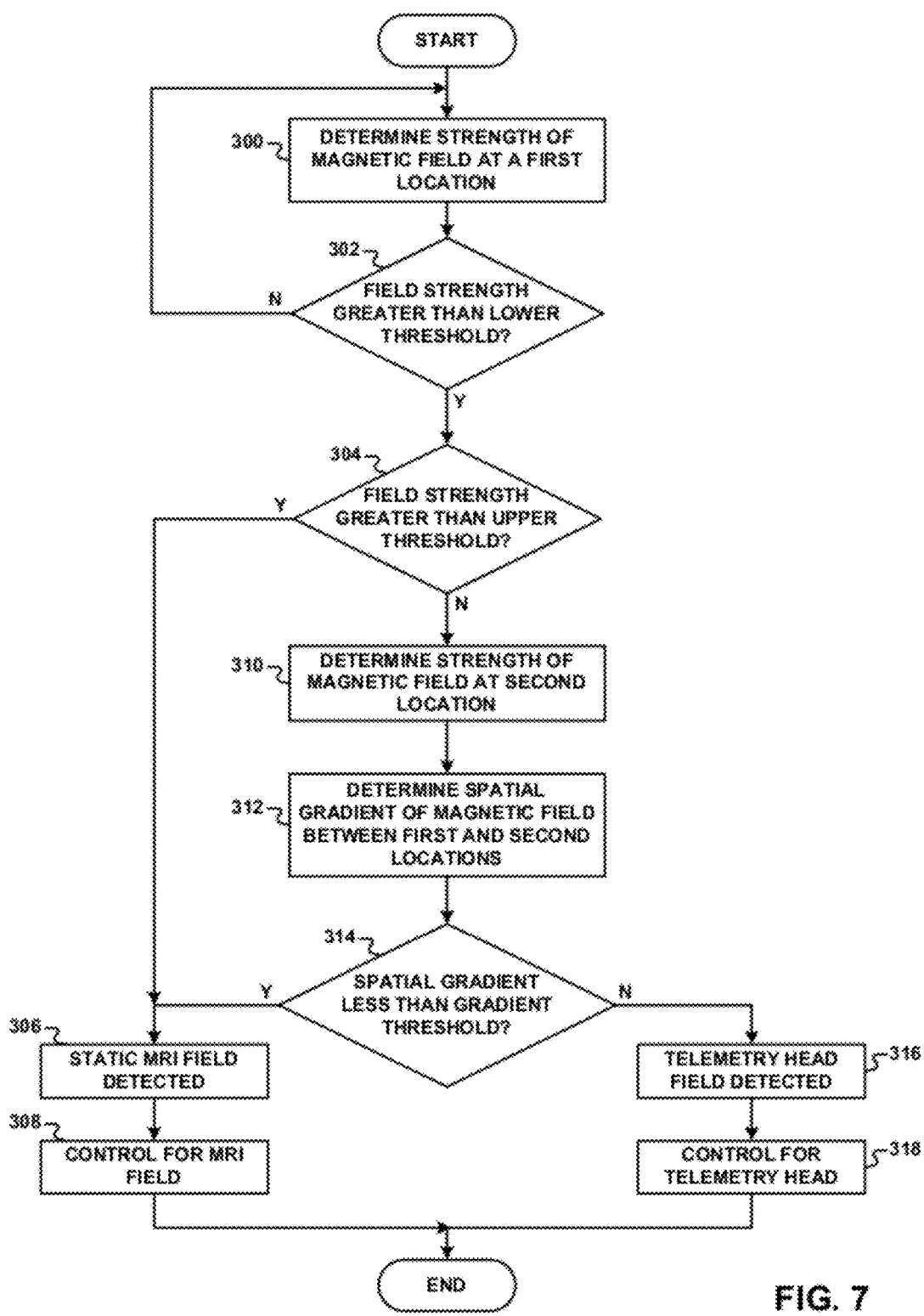
FIG. 7 illustrates an example method for differentiating between a static MRI field and a telemetry head field.

FIG. 7 illustrates an example method for differentiating between a static MRI field and a telemetry head field that may be implemented by control module 130. Initially, field measurement module 152 may determine a strength of a magnetic field at a first location based on signals received from a first one of magnetic field sensors 132 (300). Strength comparison module 154 may then compare the strength of the measured magnetic field, as determined in block (300), to the lower threshold (302). If the strength of the measured magnetic field is less than the lower threshold, field measurement module 152 may continue polling the first one of magnetic field sensors 132 in block (300) and strength comparison module 154 may indicate to processing module 140 that no magnetic field is detected. If the strength of the measured magnetic field is greater than or equal to the lower threshold, strength comparison module 154 may compare the measured magnetic field to the upper threshold (304). If the strength of the measured magnetic field is greater than or equal to the upper threshold, strength comparison module 154 may detect a static MRI field (306) (i.e., identify the source of the magnetic field as the MRI device) and indicate to processing module 140 that a static MRI field is detected. Processing module 140 may then control IMD 106 in the MRI mode (308).

If the strength of the measured magnetic field is less than the upper threshold, strength comparison module 154 may indicate to spatial gradient module 156 that the measured magnetic field strength is within the overlap region. Spatial gradient module 156 may then determine the strength of the magnetic field at a second location based on measurements taken by field measurement module 152 from a second one of magnetic field sensors 132 (310). Spatial gradient module 156 may then determine the spatial gradient of the detected magnetic field based on the strengths of the detected magnetic field at the first and second locations (312).

Spatial gradient module 156 then determines whether the spatial gradient is less than the spatial gradient threshold (314). If spatial gradient module 156 determines that the spatial gradient is less than the spatial gradient threshold, spatial gradient module 156 determines that the detected magnetic field is the static MRI field (306) and may indicate to processing module 140 that a static MRI field is detected (306). If spatial gradient module 156 determines that the spatial gradient is greater than or equal to the spatial gradient threshold, spatial gradient module 156 determines that the detected magnetic field is the telemetry head field and may indicate to processing module 140 that a telemetry head field is detected (316). Then, processing module 140 may control IMD 106 in the telemetry head mode (318).

The plurality of magnetic field sensors 132 included in IMD 106 of the present disclosure may consume more power than a single sensor typically used to detect telemetry head magnet 122. For example, a plurality of Hall-effect sensors may consume more biasing current during operation than a single Hall-effect sensor. Additionally, control module 130 may consume more processing power when determining multiple field strengths since the computation may be more mathematically intensive. Control module 130 may therefore implement a power saving strategy when processing signals from the plurality of magnetic field sensors 132. The power saving strategy may include powering a single one of the plurality of magnetic field sensors 132 until a magnetic field is detected that is stronger than the lower threshold. Then, upon initial detection of the magnetic field, control module 130 may power the remaining magnetic field sensors, process signals from the remaining magnetic field sensors, determine a spatial gradient, and identify the source of the magnetic field based on the spatial gradient.

Figure 8:
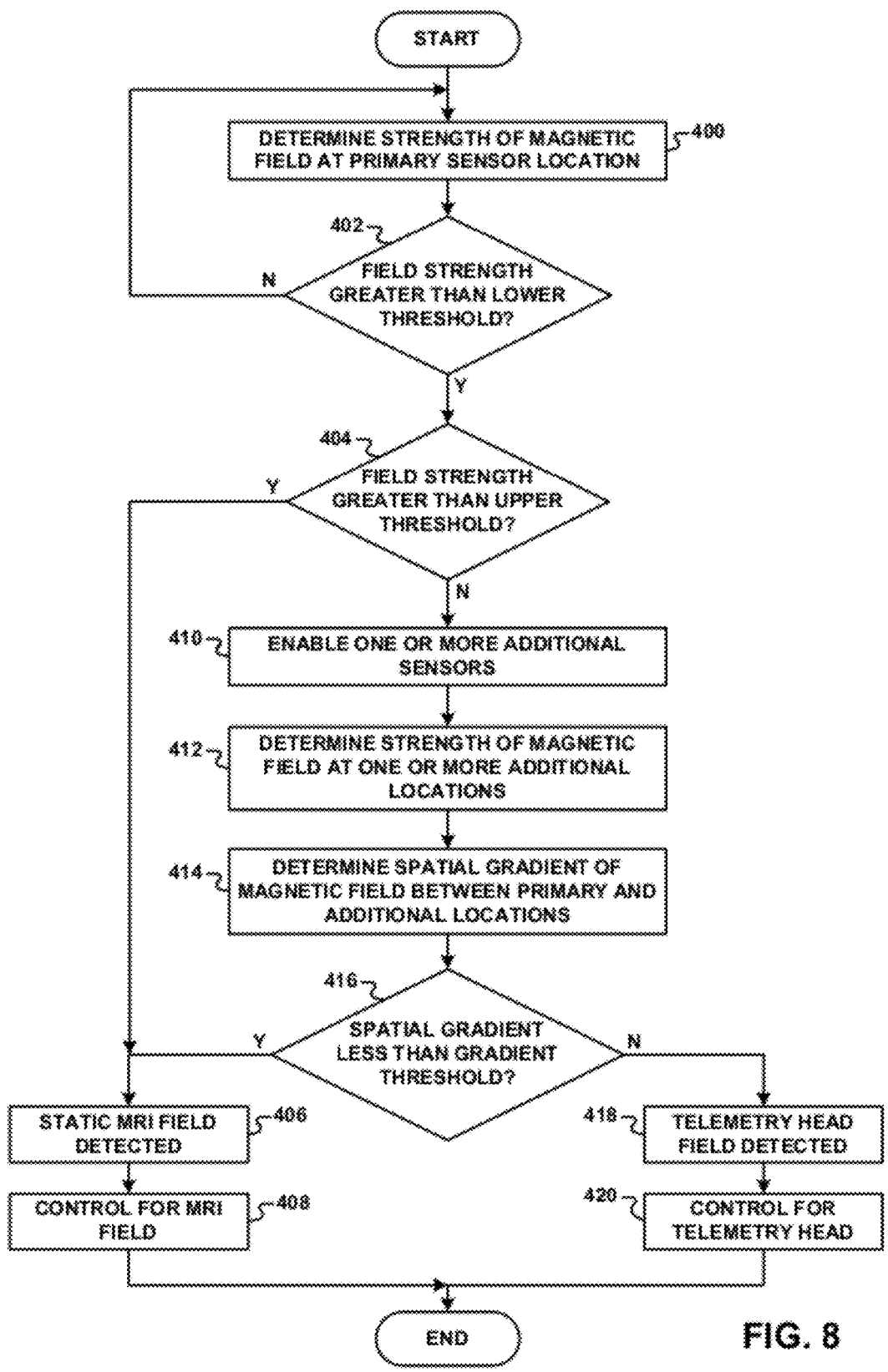
FIG. 8 illustrates a power saving strategy that may be implemented by the IMD when identifying a source of a magnetic field.

FIG. 8 is a flow chart that illustrates the power saving strategy of the present disclosure. In the method of FIG. 8, field measurement module 152 may provide power to, and receive signals from, a single one of magnetic field sensors 132. For example, field measurement module 152 may periodically, or continuously, provide power to first magnetic field sensor 132-1, receive signals from first magnetic field sensor 132-1, and measure a strength of the magnetic field at the location of first magnetic field sensor 132-1 (400). This sensor that is periodically, or continuously, used in order to initially measure the magnetic field may be referred to as a "primary sensor 132-1." Accordingly, field measurement module 152 may periodically, or continuously, provide power to primary sensor 132-1 and determine a strength of a magnetic field at the location of primary sensor 132-1.

Strength comparison module 154 may then compare the strength of the measured magnetic field to the lower threshold (402). If the strength of the measured magnetic field is less than the lower threshold, field measurement module 152 may continue reading from primary sensor 132-1, and strength comparison module 154 may indicate to processing module 154 that no magnetic field is detected. If the strength of the measured magnetic field is greater than the lower threshold, strength comparison module 154 may compare the measured magnetic field to the upper threshold (404). If the strength of the measured magnetic field is greater than or equal to the upper threshold, strength comparison module 154 may detect the static MRI field (406) and indicate to processing module that the static MRI field is detected so that processing module 140 may control IMD 106 in the MRI mode (408).

If the strength of the detected magnetic field is less than the upper threshold, strength comparison module 154 may indicate to spatial gradient module 156 that the measured magnetic field strength is within the overlap region. Additionally, field measurement module 154 may enable one or more additional sensors (410). In particular, field measurement module 154 may provide power to the additional magnetic field sensors (e.g., those sensors other than primary sensor 132-1), receive signals from the additional magnetic field sensors, and determine the strengths of the magnetic field at the locations of the additional magnetic field sensors (412).

Spatial gradient module 156 may then determine the spatial gradient of the sensed magnetic field based on the strengths of the magnetic fields at the location of primary sensor 132-1 (primary location) and the locations of the additional magnetic field sensors (i.e., additional locations) (414). Spatial gradient module 156 then identifies the source of the detected magnetic field in block (416) in a similar manner as block (314) of FIG. 7. Depending on the outcome of block (416), processing module 140 may control IMD 106 in the telemetry head mode in blocks (418)-(420) or in the MRI mode in blocks (406)-(408). In particular, in block (420) processing module 140 may control communication module 148 to communicate with telemetry head 122, e.g., download data from telemetry head 122 and upload data to telemetry head 122. In block (408), processing module 140 may execute commands that prepare IMD 106 for exposure to an MRI scan.

Various examples have been described. These and other examples are within the scope of the following claims.

The invention claimed is:

1. A device comprising:
a housing configured to be implanted in a patient;
a first magnetic field sensor located at a first location within the housing and configured to measure a first strength of a static magnetic field at the first location;
a second magnetic field sensor located at a second location within the housing and configured to measure a second strength of the static magnetic field at the second location; and
a processor configured to determine that at least one of the first and second strengths is greater than a lower threshold value and, in response to determining that at least one of the first and second strengths is greater than the lower threshold value, determine a difference between the first strength and the second strength and to identify a source of the static magnetic field based on the difference between the first and second strengths.

2. The device of claim 1, wherein the processor is further configured to:
compare the difference to a spatial gradient threshold;
identify the source of the static magnetic field as a primary magnet of a magnetic resonance imaging device when the difference is less than the spatial gradient threshold; and
identify the source of the static magnetic field as a handheld magnetic device when the difference is greater than the spatial gradient threshold.

3. The device of claim 1, wherein the processor is further configured to:
provide power to the first magnetic field sensor and inhibit power delivery to the second magnetic field sensor when the first strength is less than the lower threshold value; and
provide power to the second magnetic field sensor when the first strength is greater than the lower threshold value.

4. The device of claim 1, further comprising a third magnetic field sensor located at a third location within the housing and configured to measure a third strength of the static magnetic field at the third location, wherein the processor is configured to identify the source of the static magnetic field based on the first, second, and third strengths.

5. The device of claim 1, wherein the processor is configured to determine that neither of the first and second strengths is greater than an upper threshold value and, in response to determining that that at least one of the first and second strengths is greater than the lower threshold value and neither of the first and second strengths is greater than the upper threshold value, determine the difference between the first and second strengths.

6. The device of claim 1, wherein the processor is configured to identify the source of the static magnetic field as a magnetic resonance imaging (MRI) device when the difference is less than the spatial gradient threshold.

7. The device of claim 1, wherein the processor is further configured to determine that neither of the first and second strengths isgreater than an upper threshold value, wherein the processor determining the difference between the first and second strengths comprises the processor determining the difference between the first and second strengths in response to determining that at least one of the first and second strengths is greater than the lower threshold value and neither of the first and second strengths is greater than the upper threshold value, and wherein the processor identifying the source of the static magnetic field based on the difference between the first and second strengths comp rises the processor identifying the source of the static magnetic field as a magnetic resonance imaging (MRI) device when the difference is less than a spatial gradient threshold.

8. The device of claim 1, wherein the processor is further configured to identify the source of the static magnetic field as one of a primary magnet of a magnetic resonance imaging (MRI) device and a handheld magnetic device based on the first and second strengths.

9. The device of claim 8, wherein the processor is further configured to operate in an MRI mode during an MRI scan in response to identifying the source of the static magnetic field as the primary magnet of the MRI device.

10. The device of claim 1, wherein the processor is further configured to:
compare at least one of the first and second strengths to an upper threshold value; and
identify the source of the static magnetic field as a primary magnet of a magnetic resonance imaging (MRI) device when at least one of the first and second strengths is greater than the upper threshold value.

11. The device of claim 10, wherein the upper threshold value is greater than 100 mT.

12. The device of claim 10, wherein the processor is further configured to:
determine the difference between the first and second strengths when neither of the first and second strengths is greater than the upper threshold value;
compare the difference to a spatial gradient threshold;
identify the source of the static magnetic field as the primary magnet of the MRI device when the difference is less than the spatial gradient threshold; and
identify the source of the static magnetic field as a handheld magnetic device when the difference is greater than the spatial gradient threshold.

13. A method comprising:
measuring by a first magnetic field strength sensor a first strength of a static magnetic field at a first location within a housing of an implantable device;
measuring by a second magnetic field strength sensor a second strength of the static magnetic field at a second location within the housing of the implantable device;
determining that at least one of the first and second strengths is greater than a lower strength threshold value; and
in response to determining that at least one of the first and second strengths is greater than the lower threshold value, determining a difference between the first strength and the second strength and identifying a source of the static magnetic field based on the difference between the first and second strengths.

14. The method of claim 13, further comprising:
comparing the difference to a spatial gradient threshold;
identifying the source of the static magnetic field as a primary magnet of a magnetic resonance imaging device when the difference is less than the spatial gradient threshold; and
identifying the source of the static magnetic field as a handheld magnetic device when the difference is greater than the spatial gradient threshold.

15. The method of claim 13, further comprising:
providing power to a first magnetic field sensor while inhibiting power delivery to a second magnetic field sensor when the first strength is less than the lower threshold value; and
providing power to the second magnetic field sensor when the first strength is greater than the lower threshold value.

16. The method of claim 13, further comprising:
determining that neither of the first and second strengths is greater than an upper threshold value,
wherein determining the difference between the first and second strengths comprises determining the difference between the first and second strengths in response to determining that at least one of the first and second strengths is greater than the lower threshold value and neither of the first and second strengths is greater than the upper threshold value, and
wherein identifying the source of the static magnetic field based on the difference between the first and second strengths comprises identifying the source of the static magnetic field as a magnetic resonance imaging (MRI) device when the difference is less than a spatial gradient threshold.

17. The method of claim 13, further comprising identifying the source of the static magnetic field as one of a primary magnet of a magnetic resonance imaging (MRI) device and a handheld magnetic device based on the first and second strengths.

18. The method of claim 17, further comprising configuring the implantable device to operate in an MRI operating mode during an MRI scan in response to identifying the source of the static magnetic field as the primary magnet of the MRI device.

19. The method of claim 13, further comprising:
comparing at least one of the first and second strengths to an upper threshold value; and
identifying the source of the static magnetic field as a primary magnet of a magnetic resonance imaging (MRI) device when at least one of the first and second strengths is greater than the upper threshold value.

20. The method of claim 19, further comprising:
determining the difference between the first and second strengths when neither of the first and second strengths is greater than the upper threshold value;
comparing the difference to a spatial gradient threshold;
identifying the source of the static magnetic field as the primary magnet of the MRI device when the difference is less than the spatial gradient threshold; and
identifying the source of the static magnetic field as a handheld magnetic device when the difference is greater than the spatial gradient threshold.

21. A system comprising:
an implantable medical device (IMD);
a first magnetic field sensor connected to the IMD and configured to measure a first strength of a static magnetic field at a first location;
a second magnetic field sensor connected to the IMD and configured to measure a second strength of the static magnetic field at a second location; and
a processor configured to determine that at least one of the first and second strengths is greater than a lower threshold value and, in response to determining that at least one of the first and second strengths is greater than the lower threshold value determine a difference between the first strength and the second strength and to identify a source of the static magnetic field based on the difference between the first and second strengths.

22. The system of claim 21, wherein the processor controls a mode of operation of the IMD based on the identified source of the static magnetic field, wherein the mode of operation includes one of a telemetry head mode and magnetic resonance imaging mode.

23. The system of claim 21, wherein the IMD includes a housing, wherein the processor is included in the housing, and wherein at least one of the first and second magnetic field sensors is located within the housing.

24. The system of claim 21, wherein the IMD includes a housing, wherein the processor is included in the housing, and wherein at least one of the first and second magnetic field sensors is located outside of the housing.

25. The system of claim 21, wherein the IMD includes a lead, and wherein at least one of the first and second magnetic field sensors is connected to the lead.

26. The system of claim 21, further comprising an external computing device, wherein the processor is further configured to wirelessly communicate with the external computing device, and wherein the processor is further configured to indicate the source of the static magnetic field to the external computing device.

27. The system of claim 21, wherein the processor is further configured to determine that neither of the first and second strengths is greater than an upper threshold value,
wherein the processor determining the difference between the first and second strengths comprises the processor determining the difference between the first and second strengths in response to determining that at least one of the first and second strengths is greater than the lower threshold value and neither of the first and second strengths is greater than the upper threshold value, and
wherein the processor identifying the source of the static magnetic field based on the difference between the first and second strengths comprisesthe processor identifying the source of the static magnetic field as a magnetic resonance imaging (MRI) device when the difference is less than a spatial gradient threshold.

28. A non-transitory computer-readable storage medium comprising instructions that cause a programmable processor to:
measure by a first magnetic field strength sensor a first strength of a static magnetic field at a first location within a housing of an implantable device;
measure by a second magnetic field strength sensor a second strength of the static magnetic field at a second location within the housing of the implantable device; and
determine that at least one of the first and second strengths is greater than a lower threshold value and, in response to determining that at least one of the first and second strengths is greater than the lower threshold value, determine a difference between the first strength and the second strength and identify a source of the static magnetic field based on the difference between the first and second strengths.

29. The computer-readable storage medium of claim 28, further comprising instructions that cause the programmable processor to:
  compare the difference to a spatial gradient threshold;
  identify the source of the static magnetic field as a primary magnet of a magnetic resonance imaging device when the difference is less than the spatial gradient threshold; and
  identify the source of the static magnetic field as a handheld magnetic device when the difference is greater than the spatial gradient threshold.

30. The computer readable medium of claim 24, wherein the instructions further include determining that neither of the first and second strengths is greater than an upper threshold value, wherein determining the difference between the first and second strengths comprises determining the difference between the first and second strengths in response to determining that at least one of the first and second strengths is greater than the lower threshold value and neither of the first and second strengths is greater than the upper threshold value, and wherein identifying the source of the static magnetic field based on the difference between the first and second strengths comprises identifying the source of the static magnetic field as a magnetic resonance imaging (MRI) device when the difference is less than a spatial gradient threshold.

31. The computer-readable storage medium of claim 28, further comprising instructions that cause the programmable processor to identify the source of the static magnetic field as one of a primary magnet of a magnetic resonance imaging (MRI) device and a handheld magnetic device based on the first and second strengths.

32. The computer-readable storage medium of claim 31, further comprising instructions that cause the programmable processor to operate in an MRI operating mode during an MRI scan in response to identifying the source of the static magnetic field as the primary magnet of the MRI device.

* * * * *